US008664463B2

(12) United States Patent
Zhang et al.

(10) Patent No.: US 8,664,463 B2
(45) Date of Patent: Mar. 4, 2014

(54) REVERSIBLE ADHESIVES

(75) Inventors: Changhong Zhang, Brunswick, ME (US); Manuel Martin Orosco, Pomona, CA (US); Xiang Yu, Los Angeles, CA (US); Fikret Nuri Kirkbir, Studio City, CA (US); Mark Edward Thompson, Anaheim, CA (US)

(73) Assignee: Alfred E. Mann Institute for Biomedical Engineering at the University of Southern California, Los Angeles, CA (US)

( * ) Notice: Subject to any disclaimer, the term of this patent is extended or adjusted under 35 U.S.C. 154(b) by 268 days.

(21) Appl. No.: 13/253,775

(22) Filed: Oct. 5, 2011

(65) Prior Publication Data

US 2012/0109035 A1 May 3, 2012
US 2012/0232456 A2 Sep. 13, 2012

Related U.S. Application Data

(60) Provisional application No. 61/390,490, filed on Oct. 6, 2010.

(51) Int. Cl.
*A61F 13/00* (2006.01)
(52) U.S. Cl.
USPC .............................................. 602/41; 602/54
(58) Field of Classification Search
USPC .................................................... 602/41–54
See application file for complete search history.

(56) References Cited

U.S. PATENT DOCUMENTS

| 4,414,970 | A | 11/1983 | Berry |
| 5,412,035 | A | 5/1995 | Schmitt et al. |
| 5,752,926 | A * | 5/1998 | Larson et al. ............ 602/7 |
| 6,022,330 | A | 2/2000 | Chen et al. |
| 6,171,594 | B1 * | 1/2001 | Nielsen ................ 424/744 |
| 6,410,643 | B1 | 6/2002 | Swanson |
| 6,663,965 | B2 | 12/2003 | Poncelet |
| 7,066,182 | B1 | 6/2006 | Dunshee |
| 7,166,570 | B2 | 1/2007 | Hunter et al. |
| 7,651,680 | B2 | 1/2010 | Breton et al. |

(Continued)

FOREIGN PATENT DOCUMENTS

| WO | 2007001926 A2 | 1/2007 |
| WO | 2009097561 A1 | 8/2009 |
| WO | 2012048128 A2 | 4/2012 |

OTHER PUBLICATIONS

Silva et al. 2007. Smart Thermoresponsive Coatings, Trends in Biotechnology, pp. 577-583, vol. 25.

(Continued)

*Primary Examiner* — Michael A. Brown
(74) *Attorney, Agent, or Firm* — McDermott Will & Emery LLP

(57) ABSTRACT

This disclosure relates generally to adhesives and particularly to reversible adhesives. This disclosure further relates to generally adhesive articles and particularly to wound dressings comprising such adhesives. The adhesive comprises a core and a shell comprising at least two components. One of the components of the shell comprises a polymer formed by reacting a monomer of a thermally reversible polymer and the other component comprises a polymer formed by reacting a monomer of a polymer of a pressure sensitive adhesive. The wound dressing comprises a substrate and the reversible adhesive, forming a reversible wound dressing. Such wound dressings are particularly suitable for treatment of damaged sensitive tissue, for example wounds formed on a fragile skin.

21 Claims, 2 Drawing Sheets

(56) References Cited

U.S. PATENT DOCUMENTS

| | | | |
|---|---|---|---|
| 7,994,381 B2* | 8/2011 | Baron et al. | 602/41 |
| 8,137,392 B2* | 3/2012 | Friedensohn et al. | 607/114 |
| 2002/0028232 A1 | 3/2002 | Kubota | |
| 2004/0029994 A1 | 2/2004 | Cheng et al. | |
| 2007/0116765 A1 | 5/2007 | Hu et al. | |
| 2008/0140192 A1 | 6/2008 | Humayun et al. | |
| 2008/0311332 A1 | 12/2008 | Sakurai et al. | |
| 2009/0216170 A1 | 8/2009 | Robinson et al. | |
| 2009/0232785 A1 | 9/2009 | Breton et al. | |
| 2009/0325259 A1 | 12/2009 | Vogel et al. | |

OTHER PUBLICATIONS

Karg et al. 2006. Preparation of Thermosensitive PNIPAM Core-Shell, ChemPhysChem pp. 2298-2301, vol. 7.

Coulthard et al. 2009. Tissue Adhesives for Closure of Surgical Incisions, The Cochrane Collaboration, pp. 1-28.

International Search Report and Written Opinion of the International Searching Authority (ISA/KR), dated May 9, 2012, for PCT Application PCT/US2011/055133, filed Oct. 6, 2011 (published as WO 2012/048128 A2), which corresponds to the instant application.

* cited by examiner

REVERSIBLE ADHESIVES

CROSS-REFERENCE TO RELATED APPLICATIONS

This application is based upon and claims priority to U.S. Provisional Application Ser. No. 61/390,490, filed Oct. 6, 2010, entitled "Reversible Adhesives", the entire content of which is incorporated herein by reference.

TECHNICAL FIELD

This disclosure relates generally to adhesives and particularly to reversible adhesives. This disclosure further relates to generally adhesive articles and particularly to wound dressings comprising such adhesives.

BACKGROUND

Wound dressings incorporating pressure sensitive adhesives are well known and commercially available. Examples of wound dressings are adhesive bandages, transdermal drug patches and surgical patches.

Although such adhesives immediately adhere to a substrate when pressure is applied, their removal from the substrate becomes a hurdle later. For example, a bandage manufactured by using a pressure sensitive adhesive can easily be applied to a wound formed on a skin with high adherence. However, when this bandage is desired to be removed from the skin to replace it with another bandage or after completion of treatment of the wound, a force needs to be applied to counteract high adherence of the bandage, which may cause pain to the patient and/or damage to the wound or the healthy tissue surrounding the wound. Such hurdles are very frequently encountered during interventions to wounds by trained personnel at medical institutions as well as individuals at home.

SUMMARY

This disclosure relates generally to adhesives and particularly to reversible adhesives. This disclosure further relates to generally adhesive articles and particularly to wound dressings comprising such adhesives.

The reversible adhesive of the instant disclosure comprises a core and a shell, wherein the shell is deposited on the core. The shell comprises at least two components, a first and a second component. The first component comprises a polymer formed by reacting a monomer of a thermally reversible polymer. The second component comprises a polymer formed by reacting a monomer of a polymer of a pressure sensitive adhesive.

In one embodiment, the core comprises a chemical compound that is capable of physically incorporating water into its structure and/or capable of physically releasing the incorporated water. The core may be hydrogel, clayor mixtures thereof. In another embodiment, the core may be clay. For example, the core may be organically modified laponite clay.

The reversible adhesive may comprise at least two layers. The first layer, which is deposited on the core, comprises a polymer formed by reacting a monomer of a thermally reversible polymer. The second layer, which is deposited on the first layer (i.e. deposited after the deposition of the first layer), comprises a polymer formed by reacting a monomer of a pressure sensitive adhesive polymer. The first layer may further comprise a polymer formed by reacting a monomer of a pressure sensitive adhesive polymer. The second layer may further comprise a polymer formed by reacting a monomer of a thermally reversible polymer.

In one embodiment, the thermally reversible adhesive may be thermally reversible at a temperature within the range of 0° C. to 100° C. In another embodiment, the thermally reversible adhesive may be thermally reversible at a temperature within the range of 0° C. to 50° C.

In one embodiment, the thermally reversible polymer has a lower critical solution temperature varying within the range of 0° C. to 100° C. In another embodiment, the thermally reversible polymer has a lower critical solution temperature varying within the range of 0° C. to 50° C.

The monomer of the thermally reversible polymer may be N-isopropylacrylamide. The monomer of the pressure sensitive adhesive polymer may be a monomer of an acrylate polymer. The monomer of the pressure sensitive adhesive polymer may be ethylhexyl acrylate.

In one embodiment, the thermally reversible adhesive may adhere to a skin, an open wound or combinations thereof with an adhesive strength of higher than 0.1 N/cm$^2$ at a temperature above 35° C., as measured according to the ASTM international standard testing method number ASTM F2258-05 (2010). In another embodiment, the adhesive strength may be higher than 0.2 N/cm$^2$ at a temperature above 35° C. This adhesive strength may be negligible below 25° C. In one embodiment, the adhesive strength may be lower than 0.05 N/cm$^2$ at a temperature below 25° C. In another embodiment, the adhesive strength may be lower than 0.025 N/cm$^2$ at a temperature below 25° C.

The wound dressings of the instant disclosure comprise the reversible adhesives to provide reversible wound dressings. The wound dressings further comprise a substrate. The substrate can have any shape and structure to carry the reversible adhesive. Examples of substrates are cloths, meshes or films. At least one surface of the substrate surface may be partially or completely covered with the reversible adhesive. The remaining surface that is not covered with the adhesive can be covered with another material, for example with gauze.

In one embodiment, the wound dressings may comprise the thermally reversible adhesive to provide the thermally reversible wound dressing.

In one embodiment, the reversible wound dressings of the instant disclosure may be thermally reversible at a temperature within the range of 0° C. to 100° C. In another embodiment, the reversible wound dressings of the instant disclosure may be thermally reversible at a temperature within the range of 0° C. to 50° C.

In one embodiment, the wound dressing may adhere to a skin, an open wound or combinations thereof with an adhesive strength of higher than 0.1 N/cm$^2$ at a temperature above 35° C., as measured according to the ASTM international standard testing method number ASTM F2258-05(2010). In another embodiment, this adhesive strength may be higher than 0.2 N/cm$^2$ at a temperature above 35° C. This adhesive strength may be negligible below 25° C. In one embodiment, this adhesive strength may be lower than 0.05 N/cm$^2$ at a temperature below 25° C. In another embodiment, the adhesive strength may be lower than 0.025 N/cm$^2$ at a temperature below 25° C.

The reversible adhesives can be prepared by using different methods. One method of preparation of said adhesive comprises an emulsion polymerization method. Another method of preparation of said adhesive comprises a free radical (e.g. photochemical or thermal) polymerization method. The free radical polymerization may be carried out with or without solvent.

These, as well as other components, steps, features, objects, benefits, and advantages, will now become clear from a review of the following detailed description of illustrative embodiments, the accompanying drawings, and the claims.

BRIEF DESCRIPTION OF THE DRAWINGS

Aspects of the minimally obstructive retractor are illustrated by way of example, and not by way of limitation, in the accompanying drawings.

DETAILED DESCRIPTION OF ILLUSTRATIVE EMBODIMENTS

Figure 1:
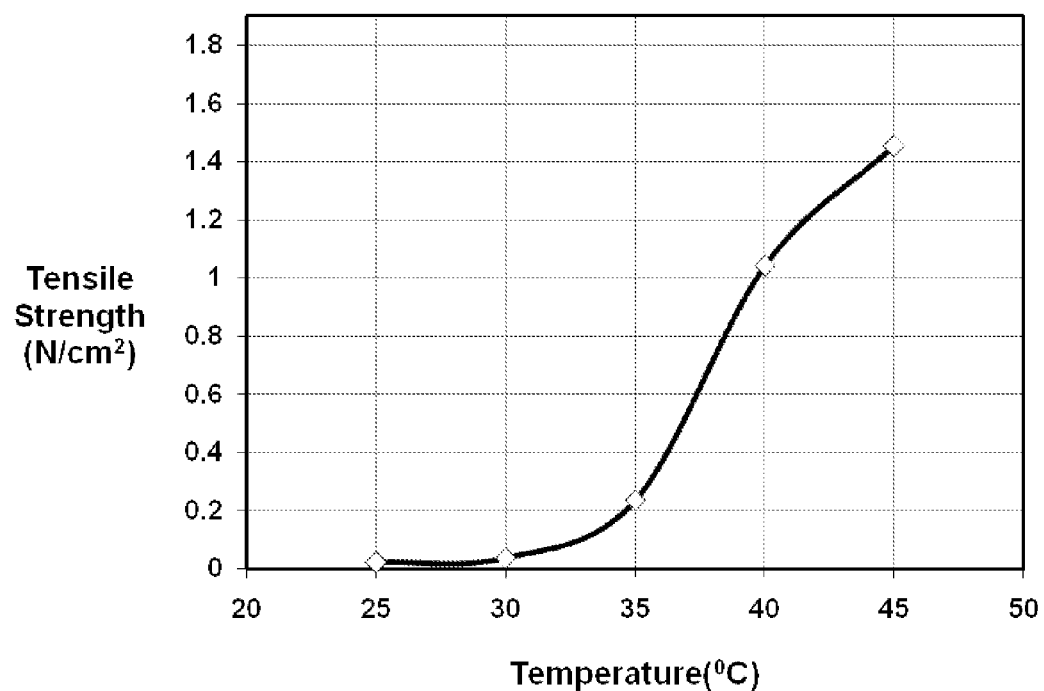
FIG. 1 shows variation of the tensile strength of a thermally reversible adhesive with temperature.

Illustrative embodiments are now discussed. Other embodiments may be used in addition or instead. Conversely, some embodiments may be practiced without all of the details which are disclosed.

This disclosure relates generally to adhesives and particularly to reversible adhesives. This disclosure further relates to preparation of such adhesives and their general applications to fields where conventional adhesives are currently used. These adhesives can particularly be applied to wound dressing field. These adhesives can also particularly be applied to wound dressings for a skin, a wound or combinations thereof. These adhesives can particularly be used to manufacture wound dressings that have reversible properties. This disclosure further relates to preparation of such wound dressings.

In one embodiment, the adhesives have improved adhesive properties or higher adhesiveness at a first predetermined condition than at a second predetermined condition. For example, these adhesives provide sufficient adhesiveness at or above a skin temperature such that a wound dressing incorporating such reversible adhesives properly adheres to skin, for example at about 37° C. (i.e. the first predetermined condition). This level of adhesiveness at or above a skin temperature is required so that, for example, the wound dressing remains adhered to the skin surrounding the wound to allow the wound to heal within a reasonable time. When this wound dressing is cooled down below 37° C., for example, by using ice (i.e. the second predetermined condition), the adhesiveness of the dressing is thereby substantially reduced to a level that the dressing can be removed from the skin with negligible force. This level of adhesiveness at a temperature below the skin temperature is required so that, for example, the wound dressing can easily be removed from the skin surrounding the wound with minimal damage to the skin and/or the wound and/or minimal pain. That is, adhesiveness of this reversible adhesive at about 37° C. is substantially higher than its adhesiveness below 37° C. In this example, the adhesive is thermally reversible at about 37° C. However, depending on type of its application, the reversible adhesive can be thermally reversible at any other temperature.

This reversibility is desired: it can be turned on or off at will making it suitable for wide variety of applications where reversibility of adhesiveness is desired or even required. The thermal reversibility is not the only mechanism by which the reversible adhesives can be manufactured. The reversibility of such adhesives can also be controlled by using other mechanisms. For example, such adhesives may provide sufficient adherence to a substrate at normal lighting conditions (e.g. sun or artificial lights). But, their adhesiveness may be reduced to a negligible level when they are irradiated by an ultraviolet (UV) light. In another example, they may provide sufficient adhesiveness to tissue at normal humidity conditions (e.g. skin humidity or weather humidity). However, they may lose their adhesiveness when sufficient amount of solvent (e.g. water, alcohol and the like) is applied. All such reversible adhesives are within the scope of this disclosure. Such adhesives hereafter will be referred to as "reversible adhesives".

In one embodiment, the reversible adhesive may adhere to a skin, an open wound or combinations thereof with an adhesive strength of higher than 0.1 N/cm$^2$ at a temperature above 35° C., as measured according to the ASTM international standard testing method number ASTM F2258-05(2010). In another embodiment, the adhesive strength may be higher than 0.2 N/cm$^2$ at a temperature above 35° C. This adhesive strength may be negligible below 25° C. In one embodiment, the adhesive strength may be lower than 0.05 N/cm$^2$ at a temperature below 25° C. In another embodiment, the adhesive strength may be lower than 0.025 N/cm$^2$ at a temperature below 25° C.

The reversible adhesives of the instant disclosure are suitable in binding any two surfaces together, for example a wood surface to a glass surface. The reversible adhesives are particularly suitable in binding a wound dressing to a tissue. The tissue can be a human tissue or a tissue of a non-human organism such as another mammal, vertebrate or microorganism. The tissue can be a living or dead cell culture. The tissue can be in any condition, e.g. it can be wet or dry.

In one particular embodiment, the tissue is skin, which is the soft outer covering of an animal, open wound or combinations thereof. That is, the reversible adhesive may provide adhesion to a skin, a wound formed on a skin or both the skin and the open wound.

In another particular embodiment, the skin is a fragile skin. Age-related changes in skin morphology in the elderly results in the development of fragile skin. With age the outer skin layer (epidermis) becomes thinner, with decreases in extracellular components, such as collagen and elastin, which leads to decrease in tensile strength and elasticity of the skin. Other age-related skin changes include thinning of the subcutaneous fat layer, increased blood vessel fragility and a decrease in the adhesiveness between the dermis and the underlying loose connective tissues, resulting in increased vulnerability to skin tears and ruptures. Fragile skin can also be induced by cancer chemo- and radiation therapy. Humans with fragile skin are prone to have wounds caused by strains inflicted on such skins at levels negligible to normal human skin. For example, a soft impact on a fragile skin by an object can easily induce a wound on a fragile skin. If such wound is covered by a commercially available typical wound dressing (e.g. an adhesive bandage) for protective or treatment purposes, the removal of the wound dressing later becomes an important problem due to considerable adherence of the wound dressing to the fragile skin. The wound dressing removal can easily cause further damage to the fragile skin or to the wound formed on such skin.

The reversible adhesives of the instant disclosure provide solutions for this important problem. The wound dressings manufactured by using the reversible adhesives can adhere to fragile skin at skin temperatures and can easily be removed with minimal force and negligible or no further damage to the skin when the wound dressing is cooled below the skin temperature, for example by using cold air, cooled compresses or ice.

Although, the wound dressings of the instant disclosure are explained above by way of the fragile skin example, they may be used in treatment of any type of wound. And all such applications are within the scope of this disclosure.

The reversible adhesives' adhesiveness may be obtained in part by using conventional adhesives such as pressure sensitive adhesives or chemical compounds used in manufacturing such conventional adhesives, but their adhesiveness is controlled or turned on or off by incorporation of reversible adhesives or chemical compounds used in manufacturing of such reversible adhesives to chemical structure or formulation of the conventional adhesives, as explained below.

In one embodiment, the reversible adhesive of the instant disclosure comprises a core and a shell, wherein the shell is deposited on the core.

The core may be any article capable of incorporating the deposition of the shell. In one embodiment, the core may comprise a chemical compound that is capable of physically incorporating water into its structure and/or capable of physically releasing the incorporated water. The core may be formed or obtained. For example, the core may be purchased from a commercial source.

In one embodiment, the core may comprise a hydrogel. For example, the hydrogel may comprise polymerization products of acrylate monomers such as 2-hydroxyethyl acrylate, 2-hydroxylethyl methacrylate, 4-hydroxybutyl acrylate, ethylene glycol methyl ether acrylate, hydroxypropyl acrylate, ethylene glycol diacrylate, N-vinylpyrrolidone or mixtures thereof. Polymerization products of such monomers may be poly(ethylene glycol) methyl ether acrylate, poly(ethylene glycol) diacrylate, polyvinylpyrrolidone or mixtures thereof. In another example, hydrogel may comprise biomaterials, such as modified gelatin, alginate, chitosan, collagen, elastin and mixtures thereof.

In another embodiment, the core may comprise clay. This clay may be nanoclay, organically modified nanoclay or mixtures thereof. This clay may be montmorillonite clay, organically modified montmorillonite clay, laponite, organically modified laponite or mixtures thereof. Organically modified clays, for example, are clays that have (meth)acrylate bonds on their surface. Such clays are commercially available, for example, from Southern Clay Products Inc. (Gonzales, Tex.).

The core may be any size, but a size at least equal to or larger than that of the chemical compound forming the core. For example, if the core comprises 2-hydroxyl ethyl methacrylate monomer, its size is at least equal to or larger than that of this monomer. Sizes of dimers, trimers, oligomers or polymers of varying molecular weight of such monomers can also form the size of the core. Or, if the core comprises particles of montmorillonite clay, its size is at least equal to or larger than that of these clay particles.

The shell may comprise at least two components, a first and a second component. The first component may comprise a polymer formed by reacting a monomer of a thermally reversible polymer and the second component may comprise a polymer formed by reacting a monomer of a pressure sensitive adhesive polymer.

In another embodiment, the shell may comprise at least two layers. At least one of these layers is deposited on the core by reacting a monomer of a thermally reversible polymer. And at least one other shell layer is deposited on the core by reacting a monomer of a pressure sensitive adhesive polymer.

Yet, in another embodiment, the shell deposited on the core comprises at least two layers. At least one of the layers may be deposited by reacting a monomer of a thermally reversible polymer and at least one of the layers may be deposited by reacting a monomer of a pressure sensitive adhesive polymer. In a further embodiment, first layer deposited on the core may be deposited by reacting a monomer of a thermally reversible polymer. In another embodiment, the first layer deposited on the core may be deposited by reacting a monomer of a polymer of a pressure sensitive adhesive. In one embodiment, second layer deposited on the first layer by reacting a monomer of a thermally reversible polymer. In another embodiment, second layer deposited on the first layer by reacting a monomer of a polymer of a pressure sensitive adhesive. In these examples, the second layer is deposited after the deposition of the first layer. All combinations of such layer depositions are within the scope of this disclosure.

For example, the thermally reversible adhesive may comprise a core and a shell, wherein the shell may comprise at least two layers; wherein the first layer, which is deposited on the core, may comprise a polymer formed by reacting a monomer of a thermally reversible polymer; and wherein the second layer, which is deposited on the first layer, may comprise a polymer formed by reacting a monomer of a pressure sensitive adhesive polymer. In such examples, the thermally reversible adhesive may have a second layer that further comprises a polymer formed by reacting a monomer of a thermally reversible polymer. Also, in such examples, the thermally reversible adhesive may even have a first layer that further comprises a polymer formed by reacting a monomer of a pressure sensitive adhesive polymer.

In one embodiment, the first layer of the shell is cohesively or chemically bonded to the core. In another embodiment, at least one layer of the shell is cohesively or chemically bonded to at least one other layer of the shell.

In this disclosure, deposition of a first article on a second article may mean formation of the second article after the formation of the first article. For example, the shell is deposited on the core may mean that the shell is formed after the core was formed or obtained. In another example, the first layer is deposited on the core may mean that the first layer is formed after the core was formed or obtained. Similarly, the second layer is deposited on the first layer may mean that the second layer is formed after the formation of the first layer.

Any individual layer forming the shell may have any thickness, but a thickness at least equal to or thicker than that of the chemical compound forming the layer. For example, if the layer comprises N-isopropylacrylamide monomer, its thickness is equal to or thicker than that of this monomer. Sizes of dimers, trimers, oligomers or polymers of varying molecular weight of such monomers can also form the thickness of each individual layer.

If a layer is thinner or thicker than a predetermined thickness, the reversible adhesive may not have desired properties. For example, if the thickness of the layer deposited by using a thermally reversible monomer is too thin or too thick, the reversible adhesive may not have sufficient adhesiveness. In another example, if the thickness of the layer deposited by using a pressure sensitive monomer is too thin or too thick, the reversible adhesive may not have sufficient reversibility. Thus, the thickness of each layer needs to be within a predetermined thickness range to obtain the reversible adhesives of the instant disclosure. For example, this thickness can be controlled by varying the composition of solution used during deposition of a particular layer on the core.

The predetermined thickness range depends on the chemical or physical properties of the chemical compound forming each layer and its value vary accordingly. This thickness may experimentally be determined for each layer.

In certain embodiments, the layer may be continuous. In other embodiment, the layer may be non-continuous. For example, the first layer after it is formed may partially cover the core. Similarly, the second layer after it is formed may partially cover the first layer. In another example, the second layer may partially cover both the first layer and the core.

Thermally reversible polymers used to prepare the reversible adhesives have novel thermal behavior in aqueous media: they have inverse solubility with increasing temperature. Their molecular structure transition from a hydrophilic to a hydrophobic structure by heating, causing them to precipitate at a higher temperature while they are completely soluble at a lower temperature. This structure change may happen rather abruptly at a temperature what is known as the lower critical solution temperature (LCST). For example, while poly(N-isopropylacrylamide) is hydrophilic and completely soluble at a temperature below LCST, it becomes hydrophobic above LCST and precipitates out of an aqueous media. For this thermally reversible polymer, LCST is in the range of 30° C. to 35° C. This polymer is adhesive to the tissue above LCST and has substantially lowered or even negligible adhesiveness below LCST.

There are many reversible polymers that can be used to prepare the reversible adhesives. Their LCST may change together with their molecular structure. Copolymers of a thermally reversible polymer with other thermally reversible polymer or any other polymer can also be prepared to obtain polymers with varying LCSTs. Thereby, LCST may be controlled at a desired level by having variety of homopolymers and copolymers and numerous reversible adhesives may be obtained for wide variety of medical or non-medical applications. All such homopolymers and copolymers are within the scope of this disclosure.

In one embodiment, the thermally reversible polymer is thermally reversible at a temperature within the range of 0° C. to 100° C. In another embodiment, the thermally reversible polymer is thermally reversible at a temperature within the range of 0° C. to 50° C.

Examples of thermally reversible polymers and their typical LCSTs are poly(N-methyl-N-n-propylacrylamide), about 19.8° C.; poly(N-n-propylacrylamide), about 21.5° C.; poly(N-methyl-N-isopropylacrylamide) about 22.3° C.; poly(N-n-propylmethacrylamide), about 28.0° C.; poly(N-isopropylacrylamide), about 30.9°; poly(N, n-diethylacrylamide), about 32.0° C.; poly(N-isopropylmethacrylamide), about 44.0° C.; poly(N-cyclopropylacrylamide), about 45.5° C.; poly(N-ethylmethyacrylamide), about 50.0° C.; poly(N-methyl-N-ethylacrylamide), about 56.0° C.; poly(N-cyclopropylmethacrylamide), about 59.0° C.; and poly(N-ethylacrylamide), about 72.0° C., and their co-polymers with other polymers, and mixtures thereof. Another example of a thermally reversible polymer is acrylate-modified tri-block copolymer of polyethylene oxide (PEO)-co-poly(p-phenylene oxide) (PPO)-co-polyethylene glycol (PEO). In the last example, the molecular ratio of each polymer can be varied to vary the LCST of the polymer. Examples of thermally reversible monomers that can be used for the purposes of the instant disclosure are the monomers used in preparation of such thermally reversible polymers.

In one embodiment, the thermally reversible polymers are polymers prepared by polymerization of monomers of N-alkylacrylamide, N-alkylmethacrylamide or mixtures thereof. One example of such monomers is N-isopropylacrylamide. And one example of such polymer is poly(N-isopropylacrylamide).

Examples of polymers of pressure sensitive adhesives are acrylate and/or methacrylate polymers, i.e. (meth)acrylate polymers, formed by polymerization of monomers such as acrylic acid, methyl acrylate, methyl methacrylate, ethylacrylate, ethyl methacrylate, propyl acrylate, propyl methacrylate, n-butyl acrylate, n-butyl methacrylate, n-pentyl acrylate, n-hexyl acrylate, n-hexyl methacrylate, n-heptyl acrylate, n-octyl acrylate, n-nonyl acrylate, lauryl acrylate, stearyl acrylate, stearyl methacrylate, behenyl acrylate, octadecylacrylate, 2-ethylhexyl acrylate and mixtures thereof.

The wound dressings may comprise the reversible adhesives to provide reversible wound dressings. In one embodiment, the wound dressings comprise the thermally reversible adhesive to provide the thermally reversible wound dressing.

The wound dressings further comprise a substrate. These substrates may have variety of shapes and structures to carry the reversible adhesive. For example the substrate can be substantially flat with relatively smooth surfaces, like polymer films; it can have a sponge like structure; and it can also have surfaces comprising filamentary structures.

Examples of substrates are cloths, meshes or films. These substrates may have variety of shapes. Examples of cloths include woven cloths such as gauze, non-woven cloths, fabrics, sponges, or composites thereof. Examples of films include films manufactured by using polymers such as polyurethane, silicone, polyimide, poly(monochloro-p-xylylene) (e.g. parylene C), poly(dimethylsiloxane) (e.g. PDMS) or films manufactured by using biologically derived materials such as elastin, alginates, chitin, collagen and fibrin. Polypeptides derived from biologic materials such as elastin may also be used. Composites of all such materials may also be used to manufacture the substrates and are thereby within the scope of this disclosure.

Gauze, non-woven cloths, fabrics and/or the like can be manufactured by using fibers such as natural fibers, synthetic fibers and composites thereof. These fibers can comprise, for example, cotton, linen, jute, hemp, cotton, wool, wood pulp, regenerated cellulosic fibers such as viscose rayon and cuprammonium rayon, modified cellulosic fibers such as cellulose acetate, synthetic fibers such as those derived from polyesters, polyamides, polyacrylics, biocompatible/biodegradable fibers such as polylactone, or composites thereof.

These substrates may be substrates used for variety of applications. For example, they may be used as surgical barriers, surgical patches (e.g., dural patches), surgical wraps (e.g., vascular, perivascular, adventitial, periadventitital wraps, and adventitial sheets), surgical dressings, meshes (e.g., perivascular meshes), bandages, tapes, tissue coverings and the like.

Examples of such substrates further include polyester, polyurethane, silicone sheet, polypropylene (PP), polyethylene (PE), polyvinyl chloride (PVC) and composites thereof. One example of the polyester polyethylene terephthalate (PET). Commercial examples of polyester films are Mylar or perforated Telfa films.

The substrate surface can be plasma treated or chemically treated to improve its bonding with the reversible adhesive. For example, such treatments may allow the attachment of vinyl bonds or functional groups to the substrate surface. In one embodiment, the reversible adhesive is cohesively or chemically bonded to the substrate. In another embodiment, the reversible adhesive further comprises a chemical compound to improve the adhesion of the reversible adhesive to the substrate. This chemical compound, for example, can be a so-called adhesion promoter. Yet, in another embodiment, the wound dressing further comprises an intermediary adhesive layer between the substrate and the reversible adhesive to improve adhesion of the reversible adhesive to the substrate. For example, this intermediary adhesive layer or primer may comprise a monomer or polymer of this monomer. For example, this monomer may be a so-called adhesion promoter.

In one embodiment, at least one surface of the substrate is partially or completely covered with the reversible adhesive.

The remaining surface that is not covered with the adhesive can be covered with another material, for example with gauze.

Although the reversible adhesives are described above by way of medical applications, these adhesives may be suitable for applications in other fields. For example, electronic, optical, electro-optical components or even automotive components, which need repairs, replacements or repositioning, may benefit from the reversible adhesives or reversible adhesive tapes manufactured by using such adhesives.

In one embodiment, the reversible wound dressings are thermally reversible at a temperature within the range of 0° C. to 100° C. In another embodiment, the reversible wound dressings are thermally reversible at a temperature within the range of 0° C. to 50° C.

In another embodiment, the reversible wound dressing adheres to a skin, an open wound or combinations thereof with an adhesive strength of higher than 0.1 N/cm$^2$ at a temperature above 35° C., as measured according to the ASTM international standard testing method number ASTM F2258-05(2010). In another embodiment, this adhesive strength may be higher than 0.2 N/cm$^2$ at a temperature above 35° C. This adhesive strength may be negligible below 25° C. In one embodiment, this adhesive strength may be lower than 0.05 N/cm$^2$ at a temperature below 25° C. In another embodiment, the adhesive strength may be lower than 0.025 N/cm$^2$ at a temperature below 25° C.

The reversible adhesives can be prepared by using different methods. One method of preparation of said adhesive comprises an emulsion polymerization method. Another method of preparation of said adhesive comprises a free radical (e.g. photochemical or thermal) polymerization method. Such polymerization may be carried out with or without solvent.

The disclosure is illustrated further by the following additional examples that are not to be construed as limiting the disclosure in scope to the specific procedures or products described in them.

Example 1

Reversible Adhesive Preparation by Emulsion Polymerization

In this example, a thermally reversible adhesive was prepared by using a water based emulsion polymerization technique as follows. First, the core was prepared. In the first step, about 0.025 gram monomer 2-hydroxyl ethyl methacrylate (HEMA) was dissolved in about 20 milliliters water to form a HEMA solution. In the second step, about 2 milliliters of about 0.135 weight % solution of initiator potassium persulfate (KPS), about 1.25 milliliters of about 1.000 weight % solution of emulsifier sodium dodecyl sulfate (SDS) were added, the solution pH was adjusted to about 9 by sodium carbonate, the reaction was performed at about 70° C.-75° C. for about 1.5 hours. (In the second step, sodium hydroxide can be used instead of sodium carbonate.) In the third step, about 0.00125 gram crosslinker N,N'-methylenebis(acrylamide) (MBA) was added to this mixture and reacted for additional 1 hour. Particles of crosslinked poly 2-hydroxyl ethyl methacrylate (pHEMA) thereby were prepared. These particles, which were suspended in water, formed the core. The size of the core was in the range of about 10 nanometers to about 30 nanometers, according to dynamic light scattering (DLS) measurement.

Then, in the fourth step, the shell was deposited on the core. First, about 0.075 gram reversible adhesive monomer N-isopropylacrylamide (NiPAM) and about 0.900 gram pressure sensitive adhesive monomer ethylhexyl acrylate (EHA) were simultaneously added and slowly mixed in a "monomer starvation mode" to the particle-water suspension, where the monomer concentration in the mixture was intentionally kept low to cause immediate polymerization of the monomer and its deposition on the core. The mixture was mixed for 2 hours. Then, to achieve complete polymerization of the monomers, 0.5 milliliter of 0.135 weight % solution of KPS was added, and this mixing was continued for another 2 hours, and another and 0.5 milliliter of 0.135 weight % solution of KPS was added, the mixing is continued for another 1 hour before the mixing was completed. All above mixings were carried out under inert atmosphere of nitrogen. The shell comprising the first component, deposited from a thermally reversible monomer NiPAM and the second component, deposited from a pressure sensitive adhesive monomer EHA, was thereby deposited on the core. The final white emulsion was coated onto a polyester (Mylar) substrate and dried in an oven at about 110° C. for about 5 minutes. An adhesive tape, i.e. wound dressing comprising a substrate and a thermally reversible adhesive, was thereby prepared.

Adhesiveness of this tape was evaluated by pressing fingertip of a human on the adhesive side of the tape. It was observed that the adhesive tape adhered to skin of the fingertip. When the tape was cooled down by pouring cold water on it or by touching an ice pack, it was observed that the tape was separated from the fingertip with substantially no effort, indicating that its adhesion to the skin was negligible.

Example 2

Reversible Adhesive Preparation by Emulsion Polymerization

In this example, the adhesive tape was prepared in the manner described in Example 1, except that about 0.025 gram HEMA, about 0.0025 gram MBA, about 0.075 gram NI, about 0.900 gram EHA, about 1.25 milliliters of about 1 weight % solution of SDS, about 2 milliliters of about 0.135 weight % solution of KPS and about 20 milliliters water were simultaneously mixed. After about 2 hours to 3 hours of polymerization, about 0.5 milliliter of about 0.135 weight % solution of KPS was added to this mixture. An emulsion was thereby obtained after about 4 hours of reaction. However, the tape showed very weak adhesion to the skin of the fingertip, indicating that the core needs to be formed before the addition of thermally reversible monomers and/or pressure sensitive adhesive monomers to have an improved adhesion to the tissue. The particle size of the emulsion was about 50 nm according to DLS measurement.

Example 3

Reversible Adhesive Preparation by Free Radical Polymerization without using any Solvent In this Example, the reversible adhesive was prepared by free radical polymerization. In this example, a bulk co-polymerization of monomers was achieved without initially forming the core and without using any solvent. About 3.7 grams N-butyl acrylate were mixed with about 0.1 gram NiPAM, about 0.2 gram HEMA and 0.02 to 0.06 gram photon initiator (Irgacure 2959 from Ciba Company), and a clear mixture was obtained. Then the liquid mixture was deposited on a polyester substrate in a nitrogen atmosphere and radiated with an ultraviolet (UV) light source, which had a power rating of about 400 W, for about 0.5 minute to about one minute to form a polymeric adhesive layer on the substrate. This substrate was immersed in water for about 12 hours to about 24 hours to remove all small molecules prior to a vacuum drying step. When the tape was cooled down by pouring cold water on it or by touching to an ice pack, it was observed that the tape was separated from the fingertip with substantially no force, indicating that its adhesion to the skin was negligible.

This example was repeated by using ethylhexyl acrylate instead of N-butyl acrylate, except that about 3.6 grams EHA, about 0.1 gram HEMA, about 0.3 gram NiPAM and 0.01 to 0.08 gram Irgacure 2959 were mixed and polymerized by the UV light source. Similar results were obtained with respect to the skin adhesion and release. The tape was adhesive to the fingertip after it was dried in the vacuum oven, but separated from the fingertip with substantially no force when the tape was cooled down by pouring cold water on it or by touching to an ice pack.

Example 4

Reversible Adhesive Preparation by using Nano Clay as Core

In this Example, the reversible adhesive was prepared by using a nano clay, montmorillonite as the core. The montmorillonite clay was purchased from Sigma-Aldrich (catalog number 139264-88-3). In the first step, about 0.04 gram clay was mixed with about 0.008 gram 2-acrylamido-2-methyl-1-propanesulfonic acid (AMPS) and about 80 milliliters water (pH about 9) for about 24 hours at room temperature with agitation to exfoliate the clay. In the second step, about 5 milliliters of about 1 weight % SDS solution and about 8 milliliters of about 0.135 weight % solution of KPS were added to the mixture at room temperature. In the third step, about 0.3 grams NiPAM and about 3.66 grams EHA were added to the mixture prepared in the second step, this mixture was heated to about 70° C. and the mixing was continued for about 5 hours to 6 hours under nitrogen. Then about 0.5 milliliter of about 0.135 weight % solution of KPS was added and the mixing was continued for about 4 hours to 5 hours to complete polymerization. The first layer of the shell was thereby deposited on the core. In the fourth step, about 0.01 gram acrylic acid (AA) and 0.1 milliliter of about 0.135 weight % solution of KPS were added to the mixture prepared in the third step and the reaction was continued for additional 1 hour at about 70° C. The second layer of the shell was thereby deposited on the first layer of the shell. The final mixture was coated onto a polyester (Mylar) substrate and dried in an oven at about 110° C. for about 5 minutes. An adhesive tape was thereby prepared.

Adhesiveness of this tape was evaluated by pressing the fingertip of a human on the adhesive side of the tape. It was observed that the adhesive tape adhered to skin of the fingertip. When the tape was cooled down by pouring cold water on it or by touching to an ice pack, it was observed that the tape was separated from the fingertip with substantially no force, indicating that its adhesion to the skin was negligible.

Example 5

In this Example, the reversible adhesive was prepared by using a clay as the core. In the first step, about 0.12 gram montmorillonite clay was mixed with about 0.024 gram AMPS in about 80 milliliter water for about 24 hours at room temperature with agitation. The pH of the solution was adjusted to about 9 by addition of sodium carbonate. In the second step, about 5 milliliters of about 1 weight % solution of SDS and about 8 milliliters of about 0.135 weight % solution of KPS were added to the mixture at room temperature. In the third step, about 0.1 gram NiPAM was added to the mixture, the reaction temperature was adjusted to 70° C. to 75° C. and the mixing was continued for about 30 minutes to form the core. In the fourth step, about 0.3 gram NiPAM and about 3.56 grams EHA were slowly added to the mixture in the monomer starvation mode in about 2 hours. After the monomer addition was completed, additional about 1 milliliter of about 0.135 weight % solution of KPS was added. This mixture was allowed to react for about 2 hours to complete polymerization. The first layer of the shell was thereby deposited on the core. In the fifth step, about 0.01 gram AA and about 0.5 milliliter of about 0.135 weight % solution of KPS solution was added to the mixture prepared in the fourth step, and the mixing was continued for about 1 hour. The second layer of the shell was thereby deposited on the first layer of the shell. The final mixture obtained in the fifth step was coated onto a polyester (Mylar) substrate and dried in an oven at about 110° C. for about 5 minutes. An adhesive tape was thereby prepared.

Adhesiveness of this tape was evaluated by pressing the fingertip of a human on the adhesive side of the tape. It was observed that the adhesive tape adhered to skin of the fingertip. When the tape was cooled down by pouring cold water on it or by touching to an ice pack, it was observed that the tape was separated from the fingertip with substantially no force, indicating that its adhesion to the skin was negligible.

Example 6

In this Example, the core was prepared by polymerization of monomer 1-vinyl-2-pyrrolidinone (VP). In the first step, about 0.04 gram VP, about 0.0047 gram N,N'-methylenebis (acrylamide) (MBA), about 5 milliliters of about 1 weight % solution of SDS, about 8 milliliters of about 0.135 weight % solution of KPS and about 80 milliliters water (pH was adjusted to about 9 by addition of sodium carbonate) were mixed. This mixture was allowed to react at about 70° C. in nitrogen atmosphere for about 1 hour. In the second step, 0.1 gram NiPAM was added to form the core particles in about 30 minutes. In the third step, about 0.2 gram NiPAM and about 3.65 grams EHA were added to the mixture prepared in the second step, and allowed to react for another 3 hours to 4 hours. During this mixing, about 0.5 milliliter of about 0.135 weight % solution of KPS was added after 2 hours to 3 hours. The first layer of the shell was thereby deposited on the core. In the fourth step, about 0.01 gram AA and about 0.1 milliliter of about 0.135 weight % solution of KPS were added to the mixture prepared in the third step at about 70° C. and the mixing was continued for about 1 hour. The second layer of the shell was thereby deposited on the first layer of the shell. The final mixture obtained in third step was coated onto a polyester (Mylar) substrate and dried in an oven at about 110° C. for about 5 minutes. An adhesive tape was thereby prepared.

Adhesiveness of this tape was evaluated by pressing the fingertip of a human on the adhesive side of the tape. It was observed that the adhesive tape adhered to skin of the fingertip. When the tape was cooled down by pouring cold water on it or by touching to an ice pack, it was observed that the tape was separated from the fingertip with substantially no force, indicating that its adhesion to the skin was negligible.

Example 7

In this Example, the core was prepared by polymerization of monomer 1-vinyl-2-pyrrolidinone (VP). In the first step, about 0.04 gram VP, about 0.0047 gram N,N'-methylenebis(acrylamide) (MBA), about 5 milliliters of about 1 weight % SDS solution, about 8 milliliters of about 0.135 weight % solution of KPS and about 80 milliliters water (pH was adjusted to about 9 by addition of sodium carbonate) were mixed. This mixture was allowed to react at about 70° C. in nitrogen atmosphere for about 1 hour. The core was thereby prepared. In the second step, about 0.3 gram NiPAM and about 3.65 grams EHA were added to the mixture prepared in the first step, and allowed to react for another 3 hours to 4 hours. Then, about 0.5 milliliters of about 0.135 weight % solution of KPS was added within 2 hours to 3 hours. The first layer of the shell was thereby deposited on the core. In the third step, about 0.01 gram AA and about 0.1 milliliter of about 0.135 weight % solution of KPS were added to the mixture prepared in the third step at about 70° C., and the mixing was continued for 1 hour. The second layer of the shell was thereby deposited on the first layer of the shell. The final mixture obtained in the third step was coated onto a polyester (Mylar) substrate and dried in an oven at about 110° C. for about 5 minutes. An adhesive tape was thereby prepared.

Adhesiveness of this tape was evaluated by pressing the fingertip of a human on the adhesive side of the tape. It was observed that the adhesive tape adhered to skin of the fingertip. When the tape was cooled down by pouring cold water on it or by touching an ice pack, it was observed that the tape was separated from the fingertip with substantially no force, indicating that its adhesion to the skin was negligible.

Example 8

In this Example, the core was prepared by polymerization of monomer 1-vinyl-2-pyrrolidinone (VP). In the first step, about 0.04 gram VP, about 0.0047 gram N,N'-methylenebis(acrylamide) (MBA), about 5 milliliters of 1 weight % SDS solution, about 8 milliliters of about 0.135 weight % solution of KPS and about 80 milliliters water (pH was adjusted to about 9 by addition of sodium carbonate) were mixed. This mixture was allowed to react at about 70° C. in nitrogen atmosphere for about 1 hour. The core was thereby prepared. In the second step, about 0.3 gram NiPAM and about 3.66 grams EHA were added to the mixture prepared in the first step, and allowed to react for another 3 hours to 4 hours. Then, about 0.5 milliliters of about 0.135 weight % solution of KPS was added and the mixing was continued for 2 hours to 3 hours. The shell comprising the first component, deposited by reacting a thermally reversible monomer NiPAM and the second component, deposited by reacting a pressure sensitive adhesive monomer EHA, was thereby deposited on the core. The final mixture obtained in the second step was coated onto a polyester (Mylar) substrate and dried in an oven at about 110° C. for about 5 minutes. An adhesive tape was thereby prepared.

Adhesiveness of this tape was evaluated by pressing the fingertip of a human on the adhesive side of the tape. It was observed that the adhesive tape adhered to skin of the fingertip. When the tape was cooled down by pouring cold water on it or by touching to an ice pack, it was observed that the tape was separated from the fingertip with substantially no force, indicating that its adhesion to the skin was negligible.

Example 9

In this Example, the core was prepared by polymerization of monomer 1-vinyl-2-pyrrolidinone (VP). In the first step, about 0.04 gram VP, about 0.0047 gram N,N'-methylenebis(acrylamide) (MBA), about 5 milliliters of about 1 weight % solution of SDS, about 8 milliliters of about 0.135 weight % solution of KPS and about 80 milliliters water (pH was adjusted to about 9 by addition of sodium carbonate) were mixed. This mixture was allowed to react at about 70° C. in nitrogen atmosphere for about 1 hour. The core was thereby prepared. In the second step, about 0.3 gram NiPAM and about 3.65 grams EHA were added to the mixture prepared in the first step, and allowed to react for another 3 hours to 4 hours. Then, about 0.5 milliliter of about 0.135 weight % solution of KPS was added and the mixing was continued for 2 hours to 3 hours. The first layer of the shell was thereby deposited on the core. In the third step, about 0.01 gram AA and about 0.1 milliliter of about 0.135 weight % solution of KPS were added to the mixture prepared in the third step at 70° C. and the mixing was continued for about 1 hours. The second layer of the shell was thereby deposited on the first layer of the shell. The final mixture obtained in the third step was coated onto a polyester (Mylar) substrate and dried in an oven at about 110° C. for about 5 minutes. An adhesive tape was thereby prepared.

Adhesiveness of this tape was evaluated by pressing the fingertip of a human on the adhesive side of the tape. It was observed that the adhesive tape adhered to skin of the fingertip. When the tape was cooled down by pouring cold water on it or by touching to an ice pack, it was observed that the tape was separated from the fingertip with substantially no force, indicating that its adhesion to the skin was negligible.

Example 10

In this Example, the core was prepared by polymerization of monomer ethylene glycol diacrylate. In the first step, about 0.04 gram ethylene glycol diacrylate, about 5 milliliters of about 1 weight % solution of SDS, about 8 milliliters of about 0.135 weight % solution of KPS and about 80 milliliters water (pH was adjusted to about 9 by addition of sodium carbonate) were mixed. This mixture was allowed to react at about 70° C. in nitrogen atmosphere for about 1 hour to form poly(ethylene glycol diacrylate (PEG) core. In the second step, about 0.3 gram NiPAM and about 3.66 grams EHA were added to the mixture prepared in the first step, and allowed to react for another 3 hours to 4 hours. Then, about 0.5 milliliters of about 0.135 weight % solution of KPS was added and the mixing was continued for 2 hours to 3 hours. The shell comprising the first component, deposited by reacting a thermally reversible monomer NiPAM and the second component, deposited by reacting a pressure sensitive adhesive monomer EHA, was thereby deposited on the core. The final mixture obtained in the second step was coated onto a polyester (Mylar) substrate and dried in an oven at about 110° C. for about 5 minutes. An adhesive tape was thereby prepared.

Adhesiveness of this tape was evaluated by pressing the fingertip of a human on the adhesive side of the tape. It was observed that the adhesive tape adhered to skin of the fingertip. When the tape was cooled down by pouring cold water on it or by touching to an ice pack, it was observed that the tape was separated from the fingertip with substantially no force, indicating that its adhesion to the skin was negligible.

Example 11

In this Example, the core was prepared by polymerization of monomer ethylene glycol diacrylate. In the first step, about 0.04 gram ethylene glycol diacrylate, about 5 milliliters of about 1 weight % solution of SDS, about 8 milliliters of about 0.135 weight % solution of KPS and about 80 milliliters water (pH was adjusted to about 9 by addition of sodium carbonate)

were mixed. This mixture was allowed to react at about 70° C. in nitrogen atmosphere for about 1 hour to form poly(ethylene glycol diacrylate (PEG). In the second step, about 0.1 gram of NiPAM was added to the mixture prepared in the first step and allowed to react for about 1 hour to form the core particles. In the third step, about 0.2 gram NiPAM and about 3.66 grams EHA were slowly added to the mixture prepared in the second step in the monomer starvation mode within 2 hours, and allowed to react for another 2 hours. About one hour after this mixing started, about 1 milliliter of about 0.135 weight % solution of KPS was added. The first layer of the shell was thereby deposited on the core. In the fourth step, about 0.5 milliliter of about 0.135 weight % solution of KPS was added, followed by about 0.01 gram acrylic acid addition and polymerization was continued for another 1 hour at about 70° C. The second layer of the shell was thereby deposited on the first layer of the shell. The final mixture obtained in the fourth step was coated onto a polyester (Mylar) substrate and dried in an oven at about 110° C. for about 5 minutes. An adhesive tape was thereby prepared.

Adhesiveness of this tape was evaluated by pressing the fingertip of a human on the adhesive side of the tape. It was observed that the adhesive tape adhered to skin of the fingertip. When the tape was cooled down by pouring cold water on it or by touching to an ice pack, it was observed that the tape was separated from the fingertip with substantially no force, indicating that its adhesion to the skin was negligible.

Example 12

In this Example, the reversible adhesive was prepared by using laponite XLS clay as the core obtained from Southern Clay Products Inc. (Gonzales, Tex.). In the first step, about 1 gram laponite XLS clay was mixed with about 100 microliters of 3-(trimethyloxysilyl)propyl methacrylate in about 900 microliters of anhydrous tetrahydrofuran (THF) and stirred for about 24 hours. The clay solution was first filtered, then washed three times with anhydrous THF, and finally dried. An organically modified clay was thereby formed as a core. In the second step, about 0.03 gram of the organically modified clay, about 3.75 milliliters of about 1 weight solution of SDS, about 2 milliliters of about 0.135 weight % solution of KPS, and about 20 milliliters of deionized water were added to a flask at room temperature. The mixture was stirred and purged with nitrogen for about 15 minutes. In the third step, about 0.2 gram NiPAM was added to the mixture, the reaction temperature was adjusted to 70° C. to 75° C. and the reaction was continued for about 30 minutes. The first layer of the shell was thereby deposited on the core. In the fourth step, about 0.2 gram NiPAM and about 3.2 grams EHA were slowly added to the mixture in the monomer starvation mode in about 2 hours. After the monomer addition was completed, additional 1 milliliter of about 0.135 weight % solution of KPS was added. This mixture was allowed to react for about 2 hours to complete the polymerization. The second layer of the shell was thereby deposited on the first layer of the shell. In the fifth step, about 0.01 gram AA and about 0.5 milliliter of about 0.135 weight solution of KPS solution were added to the mixture prepared in the fourth step, and the mixing was continued for about 1 hour. The third layer of the shell was thereby deposited on the second layer of the shell. The final white emulsion was coated onto a polyethylene terephthalate (PET) substrate and the coating was substantially dried. An adhesive tape was thereby prepared.

Adhesive strength of this tape was determined by using an ASTM international standard testing method number ASTM F2258-05(2010), entitled "Standard Test Method for Strength Properties of Tissue Adhesives in Tension". Mechanical property testing equipment, with a model number Instron 5567, manufactured by Instron (Norwood, Mass.) was used in determination of the adhesive strength. The temperature of the test samples were controlled by using an Instron temperature controlling chamber (Model Number 3119-506 Norwood, Mass.). About 2.5 cm×about 2.5 cm square of pig skin purchased from Brennen Medical, LLC (St. Paul, Minn.) was bonded to a T-shaped specimen holder, manufactured by using welded aluminum conforming to ASTM F2258-05 (2005). The pig skin was bonded on the surface of the specimen holder by using Instant Krazy Glue® Brush On, Elmer's Products, Inc. (Columbus, Ohio). The surface of the pig skin was cleaned by using about 80% alcohol solution and then dried. This cleaning was repeated for three times. The adhesive side of the adhesive tape was mounted on the cleaned surface of the pig skin. The non-adhesive side of the adhesive tape was bonded to surface of another T-shaped specimen holder, by using Krazy Glue®. Each of these two T-shaped specimen holders was placed in a grip of the testing equipment at a room temperature. Then, the temperature of the test specimen was raised to a predetermined temperature and the measurement was started. The maximum load was recorded and converted into a tensile strength (maximum load per adhesive bonded area, $N/cm^2$). Variation of the adhesive strength of the adhesive tape with temperature was shown in FIG. 1.

The measurement at each temperature was obtained by first heating the adhesive tape to about 45° C., keeping at this temperature or cooling to an appropriate temperature, and then running the test. Three samples were prepared for measurements at each temperature. The average of these three measurements was reported on FIG. 1. The results indicated that the adhesive strength significantly decreased as the testing temperature decreased. The adhesive tape adhered to the pig skin at about 45° C. When the adhesive tape was cooled by lowering the temperature from about 45° C. to about 25° C., the adhesive tape was separated from the pig skin with negligible force, indicating that its adhesion to the skin was negligible at about room temperature.

Example 13

Figure 2:
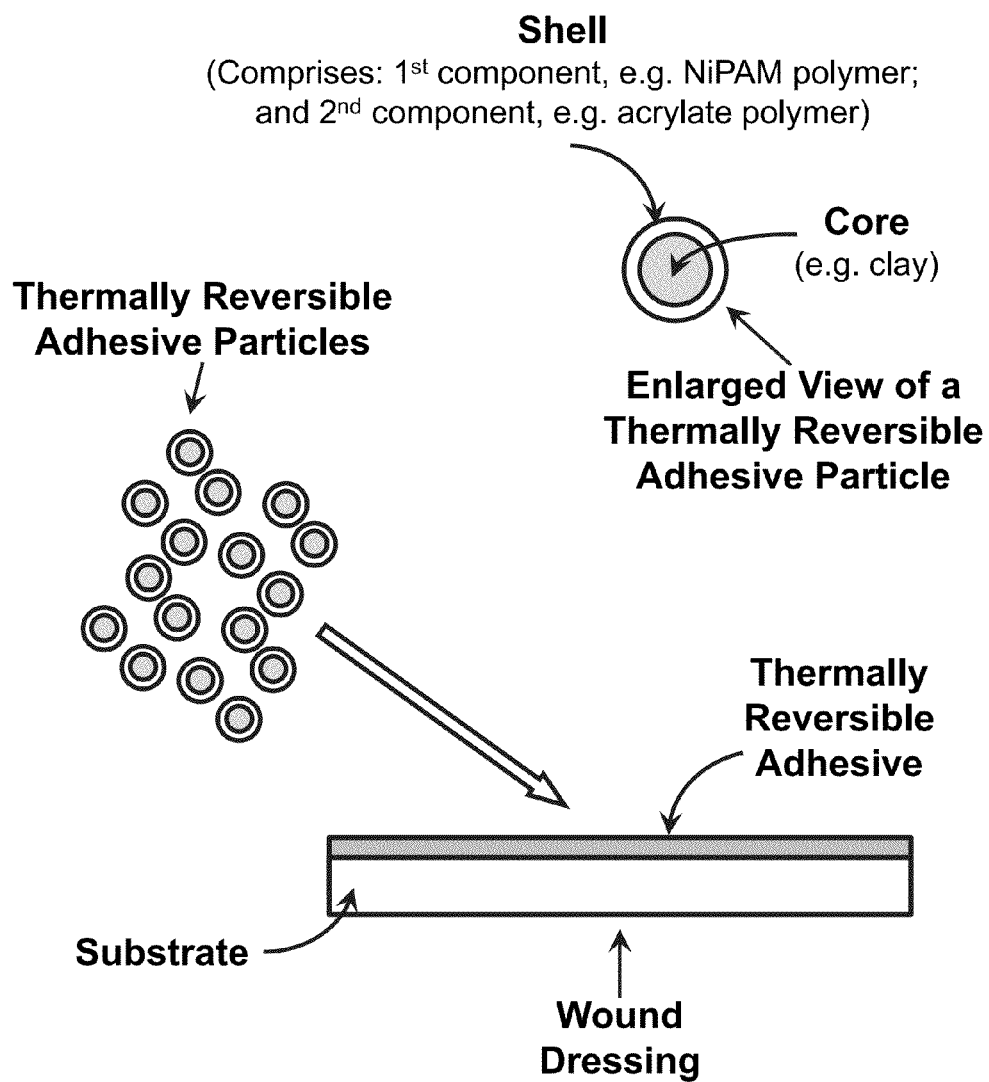
FIG. 2 shows one embodiment of the invention.

One embodiment of the invention is schematically shown in FIG. 2.

The components, steps, features, objects, benefits and advantages which have been discussed are merely illustrative. None of them, nor the discussions relating to them, are intended to limit the scope of protection in any way. Numerous other embodiments are also contemplated. These include embodiments which have fewer, additional, and/or different components, steps, features, objects, benefits and advantages. These also include embodiments in which the components and/or steps are arranged and/or ordered differently.

Unless otherwise stated, all measurements, values, ratings, positions, magnitudes, sizes, and other specifications which are set forth in this specification, including in the scope which follow, are approximate, not exact. They are intended to have a reasonable range which is consistent with the functions to which they relate and with what is customary in the art to which they pertain.

We claim:

1. A thermally reversible adhesive comprising:
   a core and a shell,
   wherein the shell is deposited on the core,
   wherein the shell comprises at least a first and a second component, wherein the first component comprises a polymer formed by reacting a monomer of a thermally reversible polymer and the second component comprises a polymer formed by reacting a monomer of a pressure sensitive adhesive polymer.

2. The thermally reversible adhesive of claim 1, wherein the core comprises a material that is capable of physically incorporating water into its structure.

3. The thermally reversible adhesive of claim 1, wherein the core is hydrogel, clay or mixtures thereof.

4. The thermally reversible adhesive of claim 1, wherein the core is clay.

5. The thermally reversible adhesive of claim 1, wherein the core is organically modified laponite clay.

6. The thermally reversible adhesive of claim 1, wherein the shell comprises at least a first and a second layer;
   wherein the first layer, is deposited on the core and comprises a polymer formed by reacting a monomer of a thermally reversible polymer; and
   wherein the second layer is deposited on the first layer and comprises a polymer formed by reacting a monomer of a pressure sensitive adhesive polymer.

7. The thermally reversible adhesive of claim 6, wherein the first layer further comprises a polymer formed by reacting a monomer of a pressure sensitive adhesive polymer.

8. The thermally reversible adhesive of claim 6, wherein the second layer further comprises a polymer formed by reacting a monomer of a thermally reversible polymer.

9. The thermally reversible adhesive of claim 6, wherein the thermally reversible adhesive further comprises a third layer, wherein the third layer is deposited on the second layer and comprises a polymer formed by reacting a monomer of a pressure sensitive adhesive polymer.

10. The thermally reversible adhesive of claim 6, wherein the monomer of a pressure sensitive adhesive polymer is acrylic acid.

11. The thermally reversible adhesive of claim 1, wherein the thermally reversible adhesive is thermally reversible at a temperature within the range of 0° C. to 100° C.

12. The thermally reversible adhesive of claim 1, wherein the thermally reversible polymer has a lower critical solution temperature varying within the range of 0° C. to 100° C.

13. The thermally reversible adhesive of claim 1, wherein the monomer of the thermally reversible polymer is N-isopropylacrylamide.

14. The thermally reversible adhesive of claim 1, wherein the monomer of the pressure sensitive adhesive polymer is a monomer of an acrylate polymer.

15. The thermally reversible adhesive of claim 1, wherein the monomer of the pressure sensitive adhesive polymer is ethylhexyl acrylate.

16. The thermally reversible adhesive of claim 1, wherein the adhesive adheres to a skin, an open wound or combinations thereof with an adhesive strength of higher than 0.1 $N/cm^2$ at a temperature above 35° C., as measured according to the ASTM international standard testing method number ASTM F2258-05(2010).

17. The thermally reversible adhesive of claim 1, wherein the adhesive adheres to a skin, an open wound or combinations thereof with an adhesive strength lower than 0.05 $N/cm^2$ at a temperature below 25° C., as measured according to the ASTM international standard testing method number ASTM F2258-05(2010).

18. A wound dressing comprising a substrate and a thermally reversible adhesive of claim 1.

19. The wound dressing of claim 18, wherein the wound dressing is thermally reversible at a temperature within the range of 0° C. to 100° C.

20. The wound dressing of claim 18, wherein the wound dressing adheres to a skin, an open wound or combinations thereof with an adhesive strength of higher than 0.1 $N/cm^2$ at a temperature above 35° C., as measured according to the ASTM international standard testing method number ASTM F2258-05(2010).

21. The wound dressing of claim 18, wherein the wound dressing adheres to a skin, an open wound or combinations thereof with an adhesive strength lower than 0.05 $N/cm^2$ at a temperature below 25° C., as measured according to the ASTM international standard testing method number ASTM F2258-05(2010).

* * * * *